United States Patent
Wada

(10) Patent No.: US 10,293,019 B2
(45) Date of Patent: May 21, 2019

(54) PHARMACEUTICAL COMPOSITION FOR TREATMENT OF OR REMISSION IN ELDERLY OR TERMINAL CANCER PATIENT

(71) Applicant: DELTA-FLY PHARMA, INC., Tokushima-shi, Tokushima (JP)

(72) Inventor: Hiromi Wada, Kyoto (JP)

(73) Assignee: DELTA-FLY PHARMA, INC., Tokushima-Shi, Tokushima (JP)

( * ) Notice: Subject to any disclaimer, the term of this patent is extended or adjusted under 35 U.S.C. 154(b) by 0 days.

(21) Appl. No.: 15/536,952

(22) PCT Filed: Nov. 25, 2015

(86) PCT No.: PCT/JP2015/083119
§ 371 (c)(1),
(2) Date: Jun. 16, 2017

(87) PCT Pub. No.: WO2016/098546
PCT Pub. Date: Jun. 23, 2016

(65) Prior Publication Data
US 2018/0256668 A1    Sep. 13, 2018

(30) Foreign Application Priority Data
Dec. 17, 2014 (JP) .................. 2014-255403

(51) Int. Cl.
*A61K 38/05* (2006.01)
*A61K 38/55* (2006.01)
*A61K 45/00* (2006.01)
*A61K 45/06* (2006.01)
*A61P 35/04* (2006.01)

(52) U.S. Cl.
CPC .............. *A61K 38/05* (2013.01); *A61K 38/55* (2013.01); *A61K 45/00* (2013.01); *A61K 45/06* (2013.01); *A61P 35/04* (2018.01)

(58) Field of Classification Search
None
See application file for complete search history.

(56) References Cited

U.S. PATENT DOCUMENTS

2004/0116354 A1* 6/2004 Ogino .................... A61K 31/00
424/278.1

FOREIGN PATENT DOCUMENTS

| EP | 1 382 349 A1 | 1/2004 | | |
|---|---|---|---|---|
| WO | WO 2011/105551 A1 | 9/2011 | | |
| WO | WO2013/037127 | * | 3/2013 | ......... A61K 2300/00 |

OTHER PUBLICATIONS

Sideras et al. Cancer inflammation and inflammatory biomarkers: can neutrophil, lymphocyte, and platelet counts represnt the complexity of the immune system? Transplant International. First Published Nov. 1, 2013, pp. 28-31. (Year: 2014).*
Liu et al. WO2013/037127, English abstract translation, Mar. 2013, 4 pages. (Year: 2013).*
Drug Interview Form, "Prescription drug anti-malignant-tumor agent Bestatin Capsule 10 mg Bestatin Capsule 30 mg," Nippon Kayaku Co., Ltd. Revised 5th Edition, Jun. 2012, pp. 1-42 (48 pages total), with a partial English translation.
Haraguchi et al., "CD13 is a therapeutic target in human liver cancer stem cells," The Journal of Clinical Investigation, vol. 120, No. 9, Sep. 2010, pp. 3326-3339.
Ichikawa et al., "Clinical Studies of Bestatin on Genitourinary Cancer," The Japanese Journal of Antibiotics, vol. 38, No. 1, Jan. 1985, pp. 166-178, with an English abstract.
International Search Report (Form PCT/ISA/210), dated Jan. 26, 2016, for International Application No. PCT/JP2015/083119.
Japanese Office Action, dated Jun. 21, 2016, for Japanese Application No. 2015-561461.
Kinugasa et al., "Old person's acute myelocytic leukemia with complication of colon cancer completely ameliorated by low dose slow induction chemotherapy," Transportation Medicine, Mar. 15, 2006, vol. 60, No. 1-2, p. 28 (4 pages total), with a partial English translation.
Labelle et al., "The initial hours of metastasis: the importance of cooperative host-tumor cell interactions during hematogenous dissemination," Cancer Discovery, vol. 2, No. 12, Dec. 2012 (published online Nov. 19, 2012), pp. 1091-1099 (10 pages total).
Liu et al., "Observation on Curative Effect of Ubenimex Tablet Combined with XELOX in Treating Colorectal Cancer," Jillin Medical Journal, vol. 35, No. 33, Nov. 2014, pp. 7385-7385 (3 pages total), with a partial English translation.
Mathé, "Bestatin, an aminopeptidase inhibitor with a multi-pharmacological function," Biomed. & Pharmacother., vol. 45, 1991, pp. 49-54.
Nakamura et al., "Two cases of oral cancer reponding to chemotherapy with UFT," Journal of Japanese Society of Oral Oncology, vol. 8, No. 1, 1996, pp. 62-66, with an English abstract.
Niimoto et al., "Prospective randomized controlled study on Beslatin in resectable gastric cancer," Biomed. & Pharmacother., vol. 45, No. 2-3, 1991, pp. 121-124.
Okimoto et al., "Bestatin Toyo ni yori Chokikan Seizon-ohu no Koganzai, Hoshasen Muko Haigan no 1 Rei," Clinical Report, vol. 26, No. 11, Sep. 1992, pp. 77-80 (5 pages total), with a partial English translation.
Saito et al., "Phase I study of Bestatin: (1) A clinical study on determination of an optimal dose of Bestatin," Cancer and Chemotherapy, vol. 10, No. 2, Part 1, 1983, pp. 211-217 (8 pages total), with a partial English translation.

(Continued)

Primary Examiner — Marcela M Cordero Garcia
(74) Attorney, Agent, or Firm — Birch, Stewart, Kolasch & Birch, LLP

(57) ABSTRACT

An object of the present invention is to provide a novel treatment method with fewer side effects for elderly cancer patients and terminal cancer patients. A pharmaceutical composition for treating or putting an elderly or a terminal cancer patient into remission, comprising, as an active ingredient, (2S)-2-[(2S,3R)-3-amino-2-hydroxy-4-phenylbutanoylamino]-4-methylpentanoic acid or a pharmacologically acceptable salt thereof.

2 Claims, 20 Drawing Sheets

(56) References Cited

OTHER PUBLICATIONS

Sugano et al., "A case of renal cell carcinoma with lymph node metastasis keeping remission for five years by adjuvant immunotherapy with ubenimex," Japanese Journal of Cancer and Chemotherapy, vol. 30, No. 10, Oct. 2003, pp. 1519-1522, with an English abstract.
Taiwanese Office Action and Search Report, dated Feb. 22, 2017, for Taiwanese Application No. 104141813.
Templeton et al., "Prognostic role of neutrophil-to-lymphocyte ratio in solid tumors: a systematic review and meta-analysis," J Natl Cancer inst., vol. 106, Issue 6, Jun. 11, 2014 (published online May 29, 2014), pp. 1-11.
Templeton et al., "Prognostic role of platelet to lymphocyte ratio in solid tumors: a systematic review and meta-analysis," Cancer Epidemiol. Biornarkers Prev., vol. 23, No. 7. Jul. 2014 (published online May 3, 2014), pp. 1204-1212 (10 pages total).
Uchibayashi et al., "Adjuvant therapy with 5-fluoro-1-(2-tetrahydrofuryl)-2,4 (1H,3H)-pyrimidinedione (UFT) and Bestatin in patients with transitional cell carcinoma of the bladder—comparison between UFT therapy alone and UFT therapy in combination with Bestatin," International Journal of Clinical Pharmacology and Therapeutics, vol. 33, No. 8, Aug. 1995, pp. 465-468.
Wakita et al., "Randomized comparison of fixed-schedule versus response-oriented individualized induction therapy and use of ubenimex during and after consolidation therapy for elderly patients with acute myeloid leukemia: the JALSG GML200 Study," Int. J. Hemalol., vol. 96, No. 1, 2012 (published online May 26, 2012), pp. 84-93 (12 pages total).
Wang el al., "Clinical effectiveness of ubenimex plus taxotere and cisplatin in the treatment of advanced non-small-cell lung cancer." Oncology Progress, vol. 8, No. 5, Sep. 2010, pp. 514-516 (4 pages total), with an English abstract.
Wang, "Clinical observation on ubenimex plus capecitabine in treatment of elderly patients with advanced colorectal cancer," J. Medical Forum, vol. 35, No. 8, Aug. 2014, pp. 29-30 (3 pages total), with an English abstract.
Bierman et al., "Partial Review of Immunotherapeutic Pharmacology in Stem Cell Transplantation," In Vivo (2000), vol. 14, pp. 221-236.
Blomgren et al., "Immunological and Haematological Monitoring in Bladder Cancer Patients Receiving Adjuvant Bestatin Treatment Following Radiation Therapy. A Prospecitve Randomized Trial," Biomedicine & Pharmacotherapy (1984), vol. 38, 143-149.
Blomgren et al., "Various Clinical Studies" In: Hamao Umezawa: "Small Molecular Immunomodifiers of Microbial Origin: Fundamental and Clinical Studies of Bestatin," Jan. 1, 1981, Japan Scientific Societies Press, Pergamon Press, pp. FP1-FP3.
Database Medline [Online] US National Library of Medicine (NLM), Bethesda, MD, US; Aug. 2003, Yasuo et al., Database Accession No. NLM12938265 (Abstract).
Extended European Search Report dated Jan. 2, 2018, in European Patent Application No. 15869754.0.
Jarstrand C. and H. Blomgren, "Increased Granulocyte Phagocytosis After Oral Administration of Bestatin, A New Immunomodulator," J. Clin. Lab. Immunol. (1982), vol. 7, pp. 115-118.
Langner et al., "Ectopeptidases: CD13/Aminopeptidase N and CD26/Dipeptidylpeptidase IV in Medicine and Biology," In: Ectopeptidases, Dec. 6, 2012, Springer US, Boston, MA, pp. 110-120.
Ota, K. and Y. Uzuka, "Clinical trials of bestatin for leukemia and solid tumors," Biotherapy (1992), vol. 4, pp. 205-214.
Ota, K., "Review of ubenimex (Bestatin): clinical research," Biomed. & Pharmacother. (1991), vol. 45, pp. 55-60.
Saito et al., "Phase I Study of Bestatin: (I) A Clinical Study for Determination of the Optimal Dose of Bestatin," In: Small Molecular Immunomodifiers of Microbial Origin, Jan. 1, 1981, Elsevier, pp. 133-141.
Watanabe et al., "Successful Treatment of a 93-Year-Old Patient with Hypoplastic Acute Monocytic Leukemia Using Macrophage Colony-Stimulating Factor," Clinical Therapeutics (1995), vol. 17, No. 1, pp. 74-81.
Blomgren et al., "The influence of Bestatin on the lymphoid system in the human," In: "Small Molecular Immunomodifiers of Microbial Origin: Fundamental and Clinical Studies of Bestatin," Edited by Hamao Umezawa, Jan. 1, 1981, Japan Scientific Press, Pergamon Press, pp. 71-99.
Examination Report No. 1 dated Feb. 1, 2018, in Australian Patent Application No. 2015364981.
Majima, H., "Phase I and Preliminary Phase II Clinical Trials of Bestatin," In: "Small Molecular Immunomodifiers of Microbial Origin: Fundamental and Clinical Studies of Bestatin," Edited by Hamao Umezawa, Jan. 1, 1981, Japan Scientific Societies Press, Pergamon Press, pp. 159-172.
Office Action dated Apr. 20, 2018, in Korean Patent Application No. 10-2017-7009847.
Sakamaki et al., "Chemotherapy with Ubenimex Corresponding to Patent Age and Organ Disorder for 18 Cases of Acute Myelogenous in Elderly Patients . . . ," Jpn. Cancer Chemother. (Aug 2003), vol. 30, No. 8, pp. 1113-1118.
Chinese Office Action for Application No. 201580001353.6, dated Dec. 17, 2018.
Lu et al., "Application of ubenimex in chemotherapy for patients with advanced ovarian cancer", Med. J. of Chinese People's Health, vol. 25, No. 13, Jul. 2013, with English language abstract.

* cited by examiner (A) Before administration (Jul-14)

(B) After administration (Nov-14)

(A)
Before administration
(Dec-14)

(B)
After administration
(Feb-15)

… (1)

PHARMACEUTICAL COMPOSITION FOR TREATMENT OF OR REMISSION IN ELDERLY OR TERMINAL CANCER PATIENT

TECHNICAL FIELD

The present invention relates to a pharmaceutical composition for treating or putting elderly cancer patients and terminal cancer patients into remission, comprising, as an active ingredient, (2S)-2-[(2S,3R)-3-amino-2-hydroxy-4-phenylbutanoylamino]-4-methylpentanoic acid or a pharmacologically acceptable salt thereof.

BACKGROUND ART

In recent years, the association of cancer aggravation with inflammatory cells and immune cells has been revealed.

A part of the mechanism on metastasis of cancer cells circulated in blood (Circulating Tumor Cells: CTCs) has been reported (Non Patent Literature 1). According to the literature, CTCs are naturally susceptible to the attack by natural killer cells (NK cells) but can avoid the attack by NK cells through attachment of a large number of platelets to the CTCs thereto. Additionally, CTCs in such condition easily adhere to the vascular endothelium, which is then activated when neutrophils are recruited in the proximity of the adhered CTCs, whereby the CTCs extravascularly transmigrate and propagate to give rise to cancer metastasis in the end.

It is also reported that there is a significant correlation between the neutrophil count (N) to lymphocyte count (L) ratio (NLR) in peripheral bloods of cancer patients and the prognosis of the cancer patients and that when the NLR is high, the prognosis is poor (Non Patent Literature 2).

Bestatin (registered trademark) is known to contain, as an active ingredient, (2S)-2-[(2S,3R)-3-amino-2-hydroxy-4-phenylbutanoylamino]-4-methylpentanoic acid (generic name: Ubenimex), binds to the aminopeptidase present on the surface of immunocompetent cells to exhibit immune reinforcement effects on cancer patients, and is approved by the Japanese authorities for the application of extending the survival time by the combined use with a maintenance and consolidation therapy agent after the remission induction of adult acute non-lymphatic leukemia and has been clinically applied (Non Patent Literature 3). It is further reported that a combination therapy, which is not applicable, has been attempted wherein, although each administration and dose is within the range of approval and authorization, a high dose of Bestatin (30 mg/day) and a high dose of UFT (400 mg/day (divided administration, twice a day)) are administered every day after surgery on bladder cancer patients, and that the combination therapy was useful when compared with UFT single administration groups (Non Patent Literature 4). It is further suggested that Bestatin is useful as a therapeutic agent for cancers with which cancer stem cells are associated, because the aminopeptidase N to which Bestatin binds is the same as the receptor (CD13) relating to the growth of cancer stem cells and the antitumor effect was confirmed when an extremely high dose (20 mg/kg) of Bestatin and a high dose (30 mg/kg) of 5-FU were administered multiple times to mice to which cancer stem cells were transplanted (Patent Literature 1 and Non Patent Literature 5).

PRIOR ART LITERATURE

Patent Literature

Patent Literature 1: WO2011/105551

Non Patent Literature

Non Patent Literature 1: Cancer Discovery, 19: 1091-1099, 2012
Non Patent Literature 2: Journal of the National Cancer Institute Review, 106(6): 124-135, 2014
Non Patent Literature 3: Drug interview Form "Prescription drug anti-malignant-tumor agent Bestatin Capsule 10 mg Bestatin Capsule 30 mg" (NIPPON KAYAKU CO., LTD., June 2012 (Revised 5th Edition))
Non Patent Literature 4: International Journal of Clinical Pharmacology and Therapeutics, 33(8): 465-468, August 1995
Non Patent Literature 5: The Journal of Clinical Investigation, 120(9): 3326-3339, 2010

SUMMARY OF INVENTION

Problem to be Solved by Invention

Today, various anticancer agents have been developed and clinically applied but many of those involve serious side effects and such therapy using the agents causes intolerable serious side effects in elderly cancer patients and terminal cancer patients in most cases. However, anticancer agents involving serious side effects are not useful any more for elderly cancer patients and terminal cancer patients but there is rather a demand for treatment methods with fewer side effects for the purpose of enhancing and maintaining QOL (Quality of Life) and extending the life.

Thus, an object of the present invention is to provide a novel treatment method suitable for elderly cancer patients and terminal cancer patients.

Means for Solving Problem

The present inventors conducted extensive studies to solve the above problems and have now found that Bestatin, which has been clinically applied exclusively in order to extend the survival time by combination with a maintenance and consolidation therapy agent after the remission induction of adult acute non-lymphatic leukemia, is useful for treating or putting elderly cancer patients and terminal cancer patients into remission when singly administered in a far lower dose than the usual dose (30 to 60 mg/body/day) to these cancer patients. The inventors have now further found that when a far lower dose of an anticancer agent or a molecular targeted drug than the usual dose is administered with a far lower dose of Bestatin than the usual dose (30 to 60 mg/body/day) which is considered not to be effective in a common sense, it is effective for treating or putting such cancer patients into remission. The present invention is based on these findings.

The present invention is as follows.

[1] A pharmaceutical composition for treating or putting an elderly or a terminal cancer patient into remission, comprising, as an active ingredient, (2S)-2-[(2S,3R)-3-amino-2-hydroxy-4-phenylbutanoylamino]-4-methylpentanoic acid or a pharmacologically acceptable salt thereof.

[2] The pharmaceutical composition according to [1], wherein the cancer patient has a high neutrophil count to lymphocyte count ratio in peripheral blood.

[3] The pharmaceutical composition according to [1] or [2], wherein the cancer patient has a high platelet count to lymphocyte count ratio in peripheral blood.

[4] The pharmaceutical composition according to any one of [1] to [3], wherein the cancer patient has a normal range of neutrophil counts in peripheral blood.

[5] The pharmaceutical composition according to any one of [1] to [4], wherein the cancer patient has a normal range of platelet counts in peripheral blood.

[6] A combination drug for treating or putting an elderly or a terminal cancer patient into remission, comprising the pharmaceutical composition according to any one of [1] to [5] and an anticancer agent and/or a molecular targeted drug.

[7] A kit preparation for treating or putting an elderly or a terminal cancer patient into remission, comprising the pharmaceutical composition according to any one of [1] to [5], an anticancer agent and/or a molecular targeted drug.

The present invention includes the disclosed contents described in Japanese Patent Application No. 2014-255403 from which the present application claims the priority.

Effect of Invention

According to the present invention, a novel treatment method with fewer side effects for elderly cancer patients and terminal cancer patients is provided.

BRIEF DESCRIPTION OF DRAWINGS

FIG. 1 is a graph showing the changes in CEA level, platelet count and CA19-9 level in peripheral blood when Bestatin is administered alone or is not administered on a 61-year-old case of the post-surgery liver metastasis of colorectal cancer.

MODE FOR CARRYING OUT THE INVENTION

Figure 1:
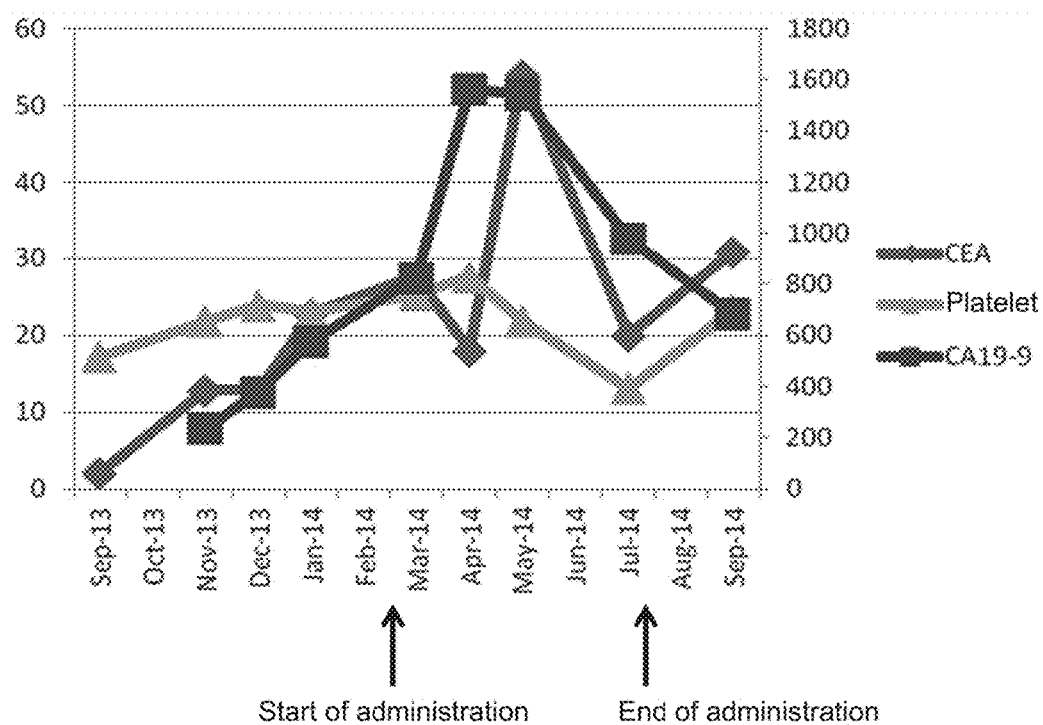
FIG. 1 This

The present invention relates to a pharmaceutical composition for treating or putting elderly cancer patients and terminal cancer patients into remission, comprising, as an active ingredient, (2S)-2-[(2S,3R)-3-amino-2-hydroxy-4-phenylbutanoylamino]-4-methylpentanoic acid or a pharmacologically acceptable salt thereof.

(2S)-2-[(2S,3R)-3-Amino-2-hydroxy-4-phenylbutanoylamino]-4-methylpentanoic acid is known under a generic name of ubenimex and is known to be usable as an active ingredient for anti-malignant-tumor agents. Hereafter, (2S)-2-[(2S,3R)-3-amino-2-hydroxy-4-phenylbutanoylamino]-4-methylpentanoic acid is written as "ubenimex" herein In the present invention, ubenimex may be produced by a conventionally known typical procedure and, for example, not only those chemically synthesized but also those produced as culture fermentation products using microorganisms can be used. Alternatively, commercial products such as "Bestatin (registered trademark)" may be used.

Ubenimex is salt free but may form a salt, as a pharmacologically acceptable salt, with, for example, hydrochloric acid, sulfuric acid or phosphoric acid.

In the present invention, the term "elderly cancer patients" means cancer patients aged 70 or more, 75 or more, 80 or more, or more than that.

Further, in the present invention, the term "terminal cancer patients" means cancer patients who are diagnosed by doctors not to be surgically operable and/or not to be treatable by any other effective standard cancer chemotherapies.

Furthermore, examples of the elderly or terminal cancer patients include those corresponding to one or more of the following (i) to (iv).
(i) The neutrophil count (N) to lymphocyte count (L) ratio (NLR) in peripheral blood is high, The "NLR is high" used herein means that such a ratio is 4 or more, more than 4, 5 or more, more than 5, 6 or more, more than 6, or more than that.
(ii) The platelet count (P) to lymphocyte count (L) ratio (PLR) is high. The "PLR is high" used herein means that such a ratio is more than 1, 1.5 or more, more than 1.5, 2 or more, more than 2, or more than that.
(iii) The platelet count in peripheral blood is within a range of typical normal values or within a range of standard values. Such a range herein can be from about 130000/μL to 350000/μL. More preferably, the platelet count in peripheral blood for the last several months (e.g., 0.5 to 3 months, preferably 1 to 2 months) is within the above range and remains on a plateau or is decreased. The "plateau" used herein means the platelet count in peripheral blood is within a range of 0 to 10% increase or decrease. The "decreased" means gradually decreasing in such a manner that the platelet count in peripheral blood decreases in a range of about 10 to 30%.
(iv) The neutrophil count in peripheral blood is within a typical value of normal values or within a range of standard values. Such a range herein can be from about 2000/mm$^3$ to 6800/mm$^3$. More preferably, the neutrophil count in peripheral blood for the last several months (e.g., 0.5 to 3 months, preferably 1 to 2 months) is within the above range and remains on a plateau or is decreased. The "plateau" used herein means the neutrophil count in peripheral blood is within a range of 0 to 10% increase or decrease. The "decreased" means gradually decreasing in such a manner that the neutrophil count in peripheral blood decreases in a range of about 10 to 30%.

In the present invention, the "cancer" means a solid cancer. The solid cancer includes any cancers except hematologic cancers such as leukemia and is not particularly limited but is preferably one or more cancers selected from lung cancers, colon or colorectal cancers, gastric or stomach cancers, breast cancers, hepatomas, pancreatic cancers, gallbladder/bile duct cancers, renal cancers, prostate cancers, bladder cancers, uterine cancers, thyroid gland cancers, duodenal cancers, and metastatic cancers thereof.

The pharmaceutical composition of the present invention, together with the active ingredient ubenimex or a pharmacologically acceptable salt thereof, may contain an excipient, a binder, a disintegrator, a lubricant, a diluent, a solubilizing auxiliary agent, a suspending agent, an isotonizing agent, a pH adjusting agent, a buffering agent, a stabilizer, a coloring agent, a flavor, and/or an odor improving agent, all of which are commonly used in pharmaceutical production, and may be in the dosage form suitable for oral administration or parenteral administration (e.g., intravenous administration, intraarterial administration, local administration by injection, intraperitoneal or intrathoracic administration, transpulmonary administration, subcutaneous administration, intramuscular administration, sublingual administration, percutaneous absorption or intrarectal administration). The pharmaceutical composition of the present invention may be formulated into solutions, emulsions, liposome preparations, injections, suspensions, ointments, creams, transdermal absorption agents, transmucosal absorption agents, tablets, pills, capsules, fine powders, powders, granules, fine granules, or syrups (not limited to these). These forms can be mixed, molded or prepared in accordance with routine methods practiced in the relevant art. The pharmaceutical composition of the present invention may be lyophilized and made into a storable form and subsequently, when used, it may be dissolved in a buffer solution containing water, physiological saline or the like and adjusted to a suitable concentration to be used.

The effects of the pharmaceutical composition of the present invention can be evaluated using one or more of the following (i) to (vii) as the indicator in patients to whom the pharmaceutical composition is administered in comparison with patients to whom the pharmaceutical composition is not administered or with patients before administration.
(i) A tumor has regressed or disappeared, or has not enlarged.
(ii) Extension of survival time (life extension effect) is confirmed.
(iii) Improvement in the cancer-associated symptoms (e.g., edema, etc.) is confirmed.
(iv) The level(s) of a tumor marker(s) in peripheral blood has/have dropped.
(v) NLR in peripheral blood has decreased.
(vi) PLR in peripheral blood has decreased.
(vii) Urinary pH has changed from acidic pH to alkaline pH.

The pharmaceutical composition of the present invention can also be used with an existing anticancer agent or a molecular targeted drug in a low dose which hardly causes critical side effects. The anticancer agents are cytocidal anticancer agents and examples include, but not limited thereto, antimetabolites (Tegafur, Tegafur/uracil (tradename: UFT), Tegafur/gimeracil/oteracil potassium combination agent, fluorouracil, gemcitabine, enocitabine, carmofur, doxifluridine, cytarabine, cytarabine ocfosfate, mercaptopurine, fludarabine, capecitabine, methotrexate, cladribine, pemetrexed, hydroxycarbamide, etc.), alkylating drugs (cyclophosphamide, thiotepa, ifosfamide, busulfan, dacarbazine, merphalan, ranimustine, nimustine, temozolomide, etc.), platinum compounds (carboplatin, cisplatin, oxaliplatin, nedaplatin, etc.), anticancer antibiotics (doxorubicin, aclarubicin, idarubicine, actinomycin D, daunorubicin, zinostatin stimalamer, bleomycin, mitomycin C, pirarubicine, epirubicin, peplomycin, amumbicine, etc.), microtubules-acting anticancer agents (vinca alkaloid, taxane, etc.) and topoisomerase inhibitors. Further, examples of the molecular targeted drug include, but not limited thereto, sorafenib, erlotinib (tradename: Tarceva), axitinib (tradename: Inlyta), everolimus, sunitinib, imatinib, lapatinib, rituximab, dasatinib, bortezomib, tamibarotene, gefitinib (tradename: Iressa.), ibritumomab, nilotinibu, temsirolimus, trastuzumab, panitumumab, tretinoin, gemtuzumab ozogamicin, crizotinib (tradename: Xalkori) and afatinib (tradename: Giotrif). One or more drugs selected from the above-described drugs can be used as the existing anticancer agents and the molecular targeted drugs.

The pharmaceutical composition of the present invention and the above existing anticancer agent and/or molecular targeted drug for combination administration can be provided as a combination product.

The "combination product" may be a combination drug comprising, as the active ingredients, the pharmaceutical composition of the present invention and the above existing anticancer agent and/or molecular targeted drug or may be those prepared, packaged and distributed in the form of a single package (kit preparation) suitable for combination administration of the antitumor agent of the present invention and the above existing cancer chemotherapeutic agent. The combination product can comprise the pharmaceutical composition of the present invention and the above existing anticancer agent and/or molecular targeted drug in a fixed ratio of the pharmaceutical composition of the present invention to the above existing anticancer agent and/or molecular targeted drug, for example, in terms of weight ratio, 1:0.01 to 1:100, for example, about 1:0.1 to 1:10, preferably about 1:0.3 to 1:3 (the pharmaceutical composition of the present invention : the above existing anticancer agent and/or molecular targeted drug).

The "combination administration" includes not only the case where the pharmaceutical composition of the present invention and the above existing anticancer agent and/or molecular targeted drug are administered simultaneously but also the case where the pharmaceutical composition of the present invention and the above existing anticancer agent and/or molecular targeted drug are administered with an interval(s) in a range within which each of the active ingredients can function simultaneously. The administration routes and the administration means of the pharmaceutical composition of the present invention and the above existing anticancer agent and/or molecular targeted drug may be identical or different.

The dose and the number of administrations of the pharmaceutical composition of the present invention may vary depending on factors such as the age and the body weight of a patient and the severity of a disease, but can be administered, in terms of the amount of the active ingredient ubenimex or a pharmacologically acceptable salt thereof, in an amount appropriately selected from a range from 1 µg to 100 mg/body/day, preferably an amount appropriately selected from 1 to 20 mg/body/day, more preferably 1 to 10 mg/body/day, 1 to 3 times a day, every day or every 1 to 21 days.

The doses of the above existing anticancer agent and/or molecular targeted drug may vary depending on factors such as the kind of active ingredients, the age and the body weight of a patient and the severity of a disease, but can be administered in an amount appropriately selected from a range from 0.0001 mg to 1000 mg/body/day 1 to 3 times a day, every day or every 1 to 14 days. For example, Tegafur/uracil (tradename: UFT), which comprise the existing anticancer agents, are administered in an amount suitably selected from 50 to 200 mg/body/day, preferably 70 to 150 mg/body/day, once a day every day. For example, erlotinib (tradename: Tarceva) as the existing molecular targeted drug is administered in an amount appropriately selected from 10 to 100 mg/body/day, preferably 20 to 60 mg/body/day, once a day every day. For example, axitinib (tradename: Inlyta) as the existing molecular targeted drug is administered in an amount suitably selected from 0,1 to 5 mg/body/day, preferably 0.5 to 3 mg/body/day, once a day every day. The above existing anticancer agents and/or molecular targeted drugs can be administered in a lower dose and more frequently than when used alone. Such an administration can prevent or delay the development of possible side effects caused by administration of the above existing anticancer agents and/or molecular targeted drugs (e.g., myelosuppression, hemolytic anemia, disseminated intravascular coagulation syndrome, fulminant hepatitis, dehydration, enteritis, interstitial pneumonia, stomatitis, gastrointestinal ulcer, gastrointestinal hemorrhage, gastrointestinal perforation, acute renal failure, mucocutaneous ocular syndrome, toxic epidermal necrolysis, neuropsychiatric disorder, acute pancreatitis, rhabdomyolysis and anosmia, but not limited to these).

The present invention further relates to a method for treating or putting elderly cancer patients and terminal cancer patients into remission using the pharmaceutical composition of the present invention. The cancer patients who can be treated or brought into remission by the method include elderly cancer patients and terminal cancer patients as defined above. The administration and doses of the pharmaceutical composition of the present invention and the existing anticancer agents and/or molecular targeted drugs in the method are as described above.

EXAMPLES

The present invention is described in more detail in reference with the following Examples. However, the present invention is not limited to these Examples.

Example 1

Single Administration of Bestatin on a 61-year-old Case of the Post-surgery Liver Metastasis of Colorectal Cancer Post-surgery liver metastasis was confirmed in the 61-year-old terminal colorectal cancer patient. Thus, a high dose of 5-FU oral anticancer agent Xeloda™ and EGFR antibody Vectibix™ were administered in combination but the level of the tumor marker CEA did not decrease but kept elevating.

Starting in March 2014 (Mar-14), Bestatin 4,10 mg/day) was administered alone every day.

As a result, the platelet count started decreasing and, in May 2014 (May-14), two months later from the Bestatin single administration started, the levels of tumor markers CEA and CA19-9 both started decreasing whereby treatment effects and improvement effects on the patient's conditions were confirmed.

However, in July 2014 (Jul-14) when the Bestatin administration was stopped due to the patient's financial reasons, the platelet count and the CEA level quickly elevated again and the patient's conditions accordingly started aggravating again.

FIG. 1 shows the measured values of the patient's CEA level, the platelet count and the CA19-9 level in peripheral blood.

Example 2

Single Administration of Bestatin on a 78-year-old Case of the Post-surgery Multiple Lung Metastases of Thyroid Gland Cancer Multiple lung metastases were confirmed in a 78-year-old thyroid gland cancer patient and the platelet count and the neutrophil count in peripheral blood both increased. In December 2013 (Dec-13), the platelet count to neutrophil count ratio (NLR) in peripheral blood was more than 5, indicating poor prognosis.

Starting in March 2014 (Mar-14), Bestatin (10 mg/day) was administered alone every day.

As a result, drops in the platelet count and the neutrophil count in peripheral blood, and drop and improvement in the NLR value, were confirmed.

Table 1 below shows the measured values of the patient's leukocytes count, neutrophil count, and lymphocyte count in peripheral blood and NLR before and after the Bestatin single administration.

TABLE 1

| | 2014 Jan. 10 (Before administration) | 2014 Jul. 15 (After administration) |
|---|---|---|
| Leukocyte | 9500 | 4900 |
| Neutrophil | 83% | 55% |
| Lymphocyte | 8% | 22% |
| NLR | 10.0 | 2.5 |

Example 3

Bestatin Single Administration on a 61-year-old Case of the Post-surgery Recurrence of Non-small Cell Lung Cancer The 61-year-old non-small cell lung cancer patient received lung right upper lobectomy, then immunotherapy, but enlargement of the right cervical lymph node was confirmed (September 2012 (Sep-12)). Subsequently, the elevation of CEA levels in peripheral blood was confirmed.

Starting in January 2014 (Jan-14), Bestatin (10 mg/day) was administered alone every day.

As a result, a drop in the CEA leveleripher blood was confirmed.

Figure 2:
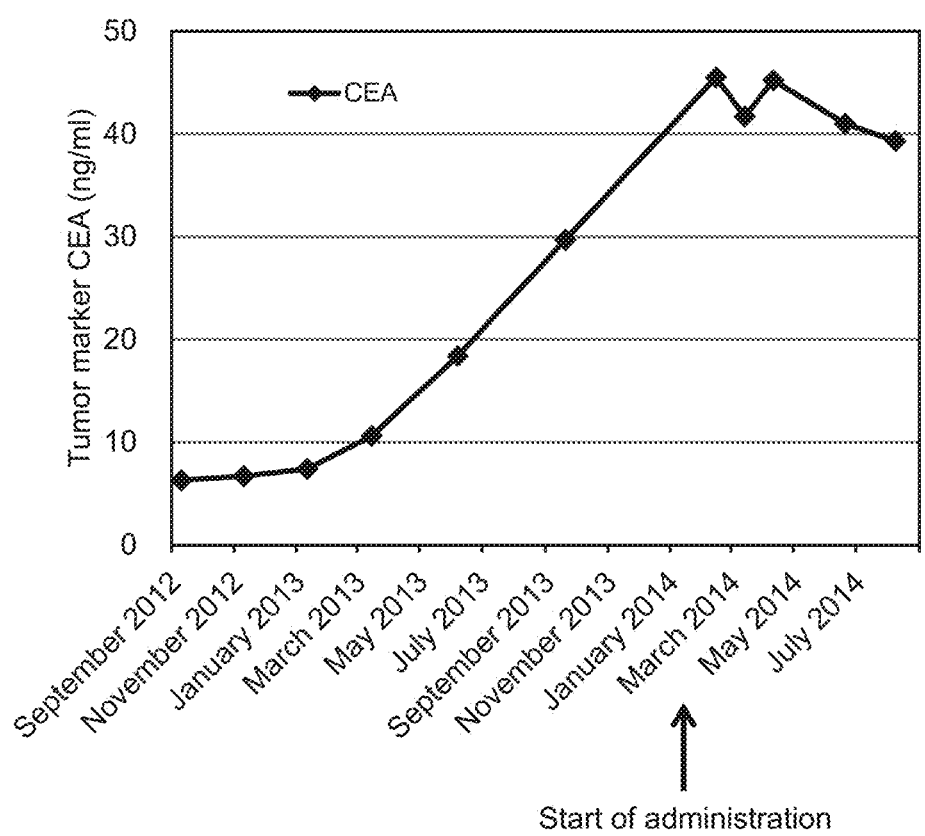
FIG. 2 This figure is a graph showing the changes in CEA level in peripheral blood by single administration of Bestatin on a 61-year-old case of the post-surgery recurrence of non-small cell lung cancer.

FIG. 2 shows the measured values of the patient's CEA levels in peripheral blood.

Example 4

Combination Administration of Bestatin and Anticancer Agent (Tradename, UFT) on an 82-year-old Case of Non-small Cell Lung Cancer Bestatin (10 mg/day) and UFT (100 mg/day) were administered once a day every day for 2 months to an 82-year-old non-small cell lung cancer patient (duodenal cancer completely recovered 5 years ago). The UFT dose used herein was an extremely low dose of one third to one sixth of the commonly used dose.

As a result, a drop and improvement in the NLR value were confirmed after the start of administration (dropped from about 5 to 2) whereby the patient's prognosis was expected to improve.

Figure 3:
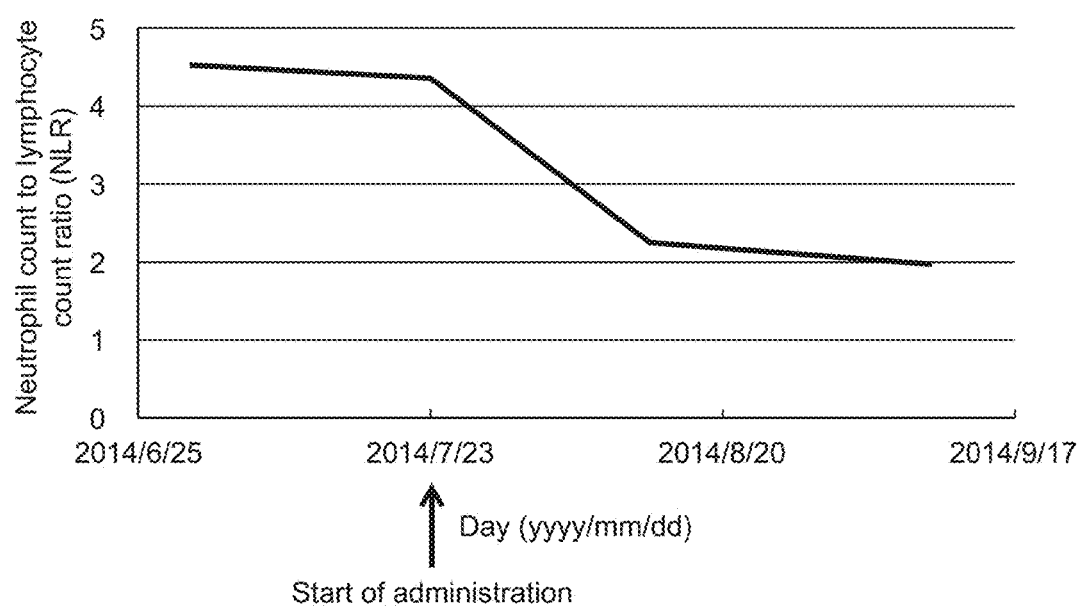
FIG. 3 This figure is a graph showing the changes in NLR in peripheral blood by combination administration of Bestatin and an anticancer agent (LIFT) on an 82-year-old case of non-small cell lung cancer.

FIG. 3 shows the measured values of the patient's NLR.

Example 5

Combination Administration of Bestatin and Molecular Targeted Drug (Tarceva™) on a 71-year-old Case of the Multiple Liver Metastases of Duodenal Papilla Cancer Bestatin (20 mg/day) and Tarceva™ (25 mg/day) were administered once a day every day for 1 month to a 71-year-old duodenal papilla cancer patient with liver metastases. The Tarceva dose used herein was an extremely low dose of one sixth of the commonly used dose.

As a result, in regard with tumor markers in peripheral blood after the start of administration, CEA remained unchanged but CA72-4 and NCC-ST-439 were confirmed to have decreased whereby treatment effects and improvement effects on the patient's conditions were confirmed.

Table 2 below shows the measured values of the patient's CEA, CA72-4 and NCC-ST-439 levels in peripheral blood before and after combination administration of the Bestatin and Tarceva™.

TABLE 2

| | 2014 Jun. 19 (Before administration) | 2014 Sep. 25 (After administration) |
|---|---|---|
| CEA | 14.0 | 13.9 |
| CA72-4 | 33.3 | 20.8 |
| NCC-ST-439 | 89.0 | 64.0 |

Figure 9:
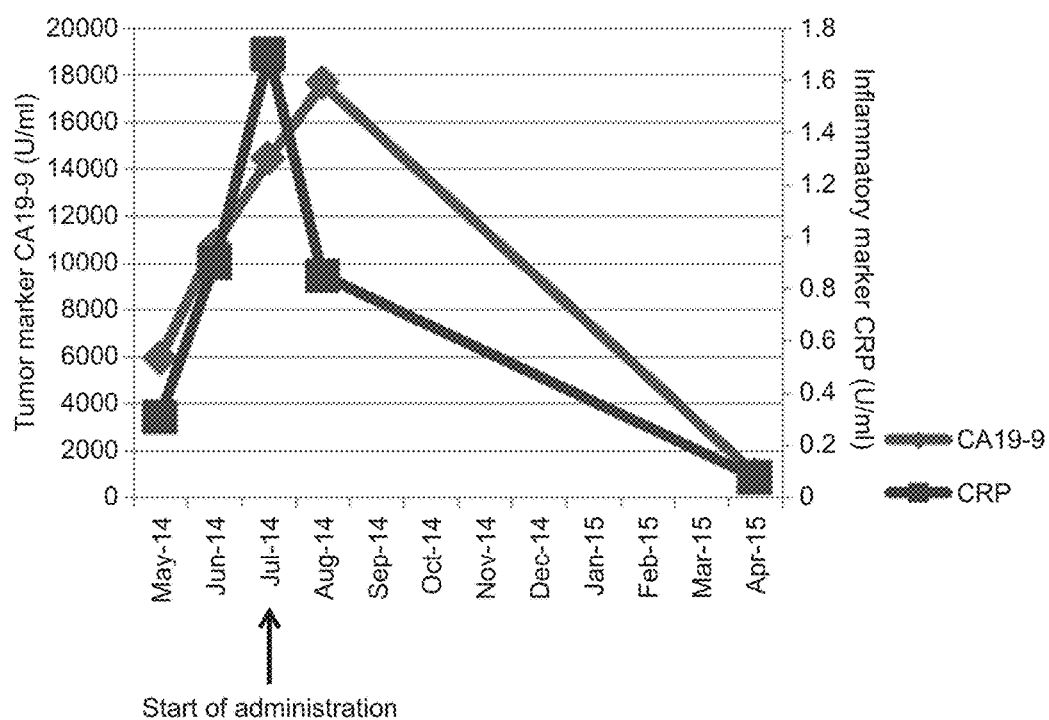
FIG. 9 This figure is a graph showing the changes in CA19-9 and CRP in peripheral blood by combination administration of Bestatin and a molecular targeted drug (Tarceva™) on a 71-year-old case of the multiple liver metastases of duodenal papilla cancer.
Figure 10:
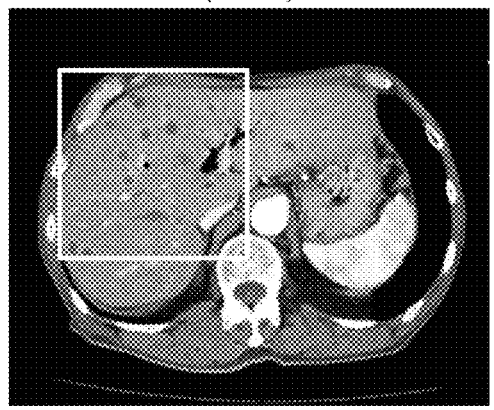
FIG. 10 This figure is photo images (CT diagnostic images) showing the focus before (A) and after (B) combination administration of Bestatin and a molecular targeted drug (Tarceva™) on a 71-year-old case of the multiple liver metastases of duodenal papilla cancer. The square shows the region where treatment effects were notably confirmed.
Figure 10:
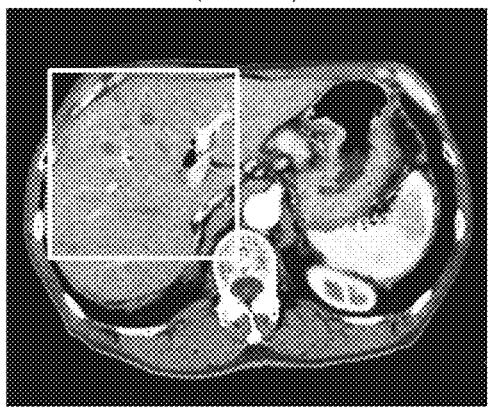

Further, FIG. 9 below shows the measured values of the patient's CA19-9 and CRP in peripheral blood before and after combination administration of Bestatin and Tarceva™. After the start of administration, drops in both the tumor markers CA19-9 and CRP values were confirmed. Further, the size and number of the metastatic cancers in the liver were found to have reduced (FIG. 10) whereby treatment effects and improvement effects on the patient's conditions were confirmed.

Example 6

Combination Administration of Bestatin and Molecular Targeted Drug (Inlyta™) on a 77-year-old Case of Renal Sarcoma Bestatin (10 mg/day) and Inlyta™ (2 mg/day) were started to be administered once a day every day (Jul. 25, 2014) to a 77-year-old renal sarcoma patient. The Inlyta™ dose used herein is an extremely low dose of one fifth of the commonly used dose, Subsequently (Aug. 18, 2014), as stomatitis was confirmed, the Inlyta™ dose was changed to 1 mg/day and the Bestatin dose was changed to 20 mg/day.

As a result, a drop and improvement in the platelet count to lymphocyte count ratio (PLR) value (dropped from about 2 to 1) were confirmed since the start of administration whereby the patient's prognosis was confirmed to have been improved. Additionally, edema on both legs started subsiding (Aug. 23, 2014) and disappeared in the end.

Figure 4:
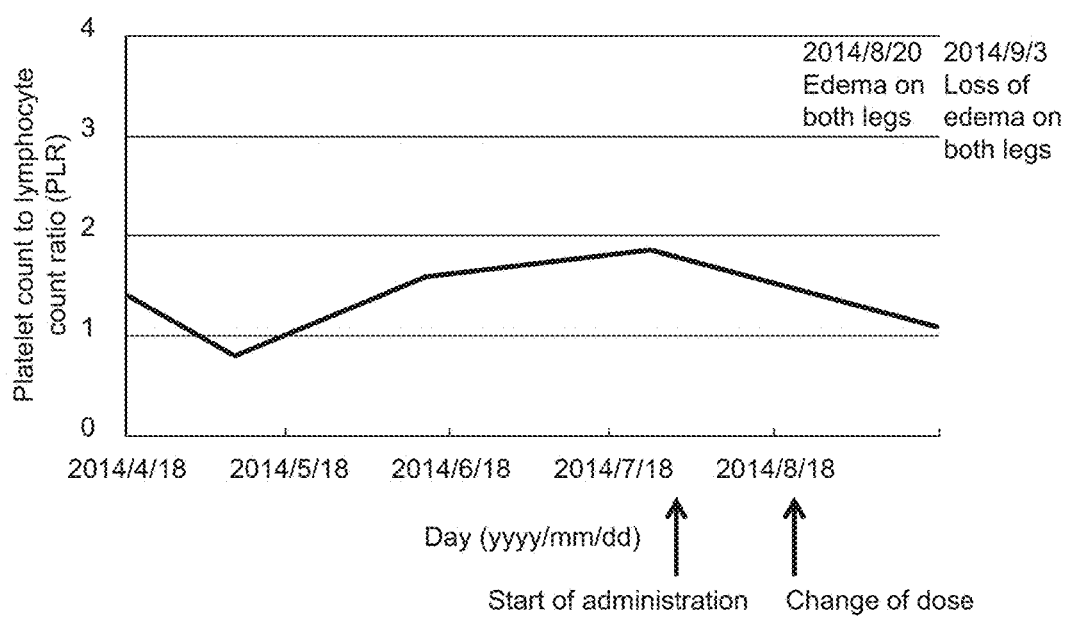
FIG. 4 This figure is a graph showing the changes in platelet count to lymphocyte count ratio (PLR) in peripheral blood by combination administration of Bestatin and a molecular targeted drug (Inlyta™) on a 77-year-old case of renal sarcoma.

FIG. 4 shows the measured values of the patient's PLR.

Example 7

Combination Administration of Bestatin and Molecular Targeted Drug (Tarceva™) c on a 50-year-old Case of Non-small Cell Lung Cancer Bestatin (10 mg/day) and Tarceva™ (50 mg/day) were administered once a day every day to a 50-year-old terminal intractable non-small cell lung cancer patient (having a variation in Epidermal Growth Factor Receptor; EGFR). The dose of Tarceva™ used here is an extremely low dose of about one third of the commonly used dose.

As a result, drastic drops in levels of tumor markers (CEA and SLX) were confirmed in the non-small cell lung cancer patient having a variation in EGFR for which effects could hardly be achieved/expected.

Table 3 below shows the measured values of the patient's CEA and SLX before and after the combination administration of Bestatin and Tarceva™.

TABLE 3

|  | 2014 Apr. 10 (Before administration) | 2014 Sep. 2 (After administration) |
|---|---|---|
| CEA | 2252.2 | 43.3 |
| SLX | 5897.5 | 94.3 |

Example 8

Combination Administration of Bestatin and Molecular Targeted Drug (Iressa™) on a 57-year-old Case of the Multiple Bone Metastases of Non-small Cell Lung Cancer Bestatin (10 mg/day) and Iressa™ (250 mg/day) were administered starting in October, 2013 once a day every day to a 57-year-old terminal intractable non-small cell lung cancer patient (having a variation in EGFR, with pleurisy/pleural effusion and metastases to the backbone and pelvis).

As a result, drops in levels of NLR and inflammatory marker C-reactive protein (CRP) were confirmed in the non-small cell lung cancer patient having a variation in EGFR for which effects could hardly be achieved/expected.

Figure 5:
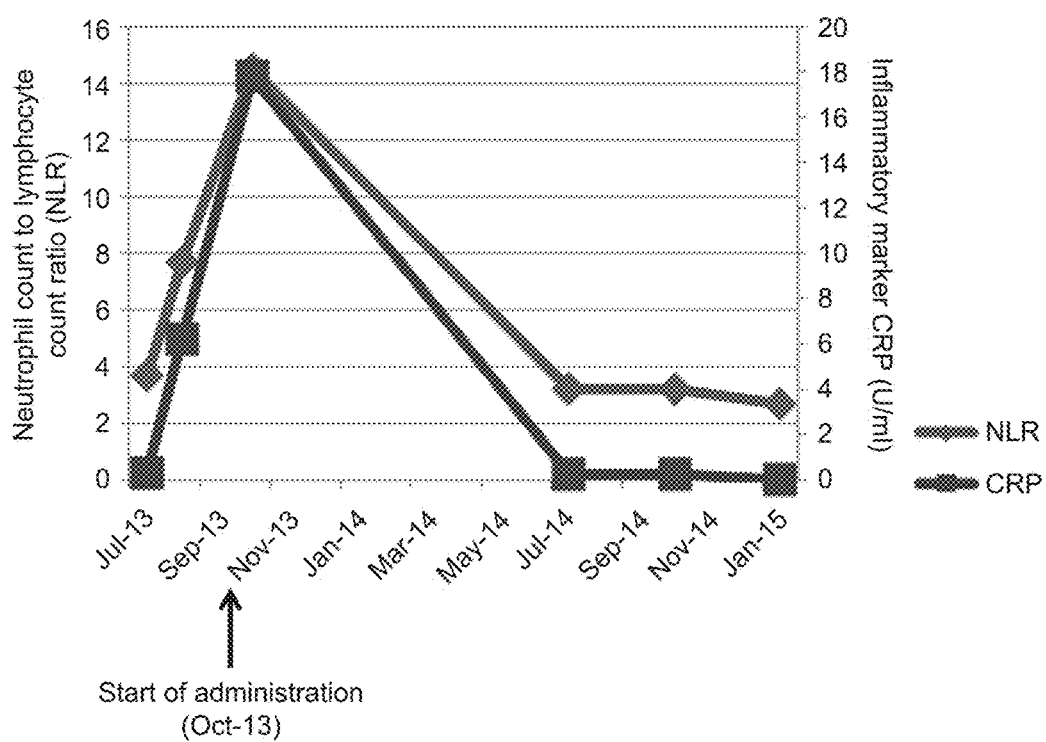
FIG. 5 This figure is a graph showing the changes in NLR and CRP in peripheral blood by combination administration of Bestatin and a molecular targeted drug (Iressa™) on a 57-year-old case of the multiple bone metastases of non-small cell lung cancer.

FIG. 5 shows the measured values of the patient's NLR and CRP.

Figure 6:
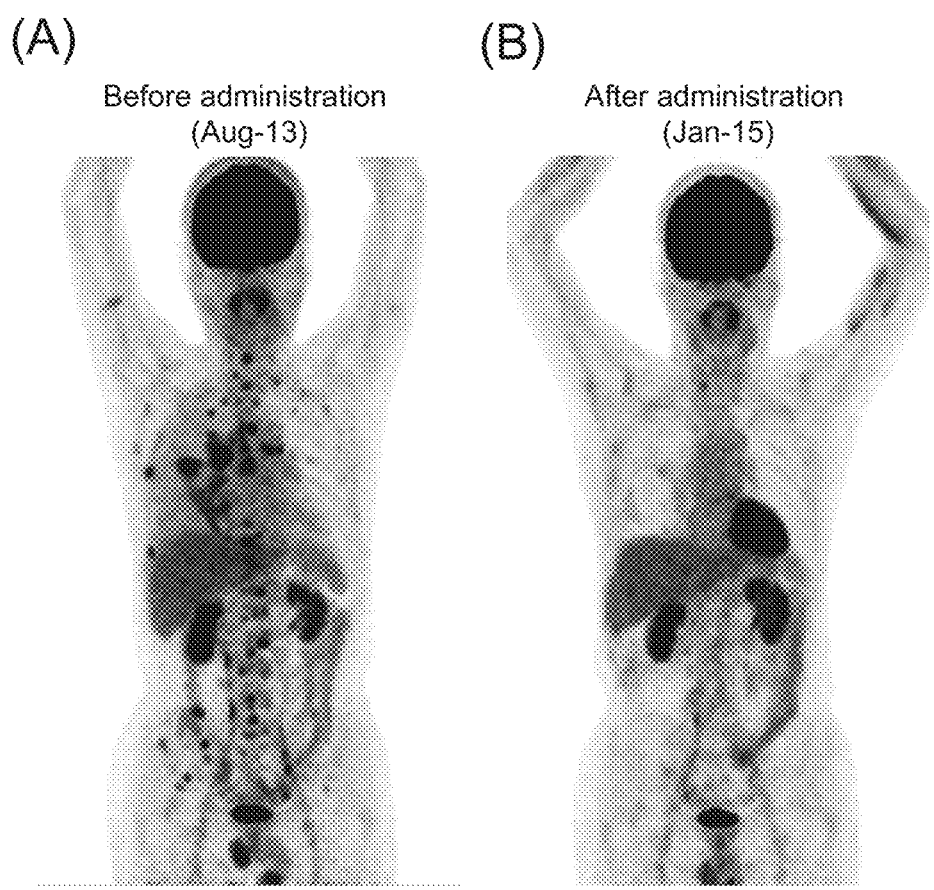
FIG. 6 This figure is photo images (PET diagnostic images) showing the focuses before (A) and after (B) combination administration of Bestatin and a molecular targeted drug (Iressa™) on a 57-year-old case of the multiple bone metastases of non-small cell lung cancer.

Further, all metastatic cancers at sites including the backbone and pelvis were found to have disappeared (FIG. 6: PET diagnostic images).

Example 9

Combination Administration of Bestatin and Molecular Targeted Drug (Tarceva™) on a 49-year-old Case of the Multiple Bone Metastases of Lung Adenocarcinoma The 49-year-old terminal lung adenocarcinoma patient (having a variation in EGFR, with metastases to the backbone, pelvis, etc.) received the cisplatin/pemetrexed therapy and the CEA level in peripheral blood kept dropping but as the elevation was confirmed (Jun. 16, 2014), Bestatin (10 mg/day) and Tarceva™ (50 mg/day) administration was started once a day every day (Jul. 16, 2014), As a result, it was confirmed that the patient's tumor marker CEA level dropped and did not elevate thereafter. Further, the urine pH value was found to have elevated since the start of administration.

Figure 7:
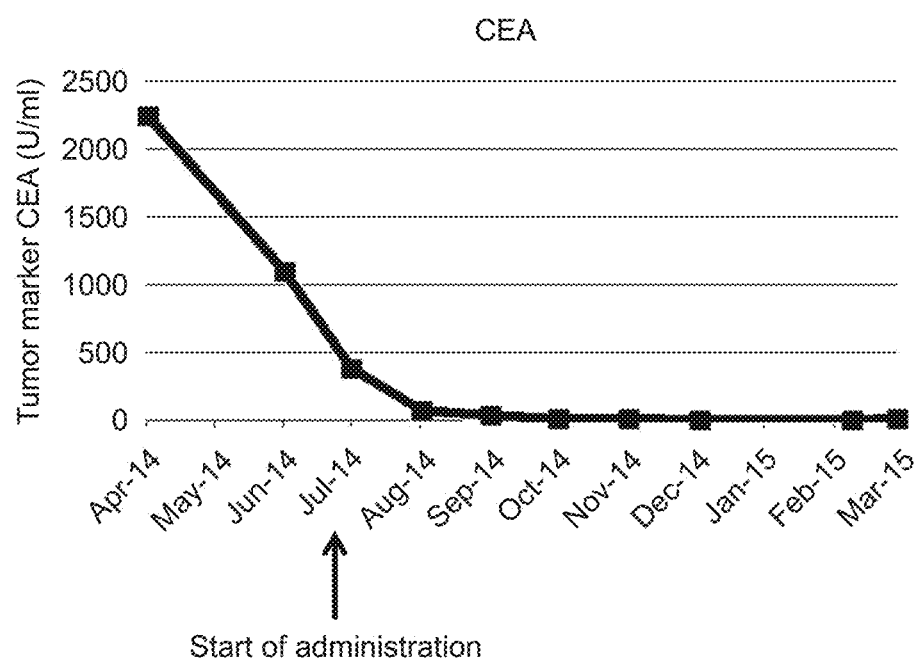
FIG. 7 This figure is a graph showing the changes in CEA in peripheral blood by combination administration of Bestatin and a molecular targeted drug (Tarceva™) on a 49-year-old case of the multiple bone metastases of lung adenocarcinoma.

FIG. 7 shows the measured values of the patient's CEA in peripheral blood.

Figure 8:
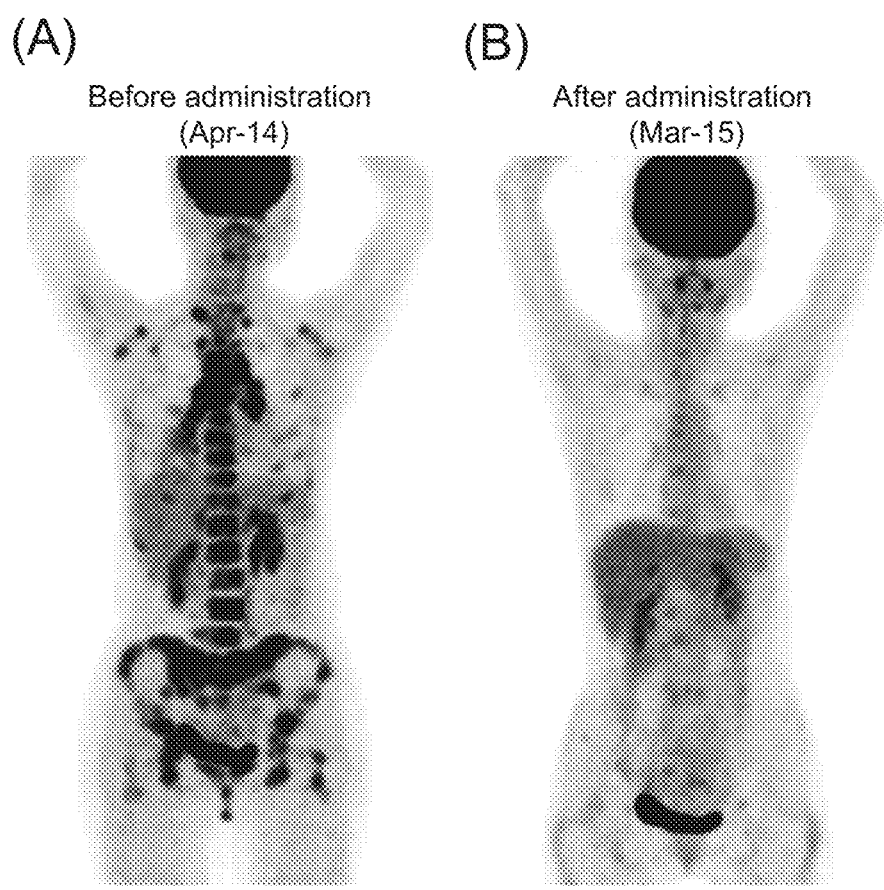
FIG. 8 This figure is photo images (PET diagnostic images) showing the focuses before (A) and after (B) combination administration of Bestatin and a molecular targeted drug (Tarceva™) on a 49-year-old case of the multiple bone metastases of lung adenocarcinoma.

Further, all metastatic cancers at sites including the backbone and pelvis were found to have disappeared (FIG. 8: PET diagnostic images).

Example 10

Combination Administration of Bestatin and Molecular Targeted Drug (Xalkori™) on a 30-year-old Case of the Carcinomatous Pleurisy and Carcinomatous Pericarditis of Lung Cancer Bestatin (10 mg/day) and Xalkori™ (250 mg/day) were administered once a day every day to a 30-year-old terminal intractable non-small cell lung cancer patient (having a variation in EGFR, with carcinomatous pleurisy and carcinomatous pericarditis and metastases to the cervical lymph node, spleen and ribs). The administration period was 14 months from September 2013 to November 2014.

Figure 11:
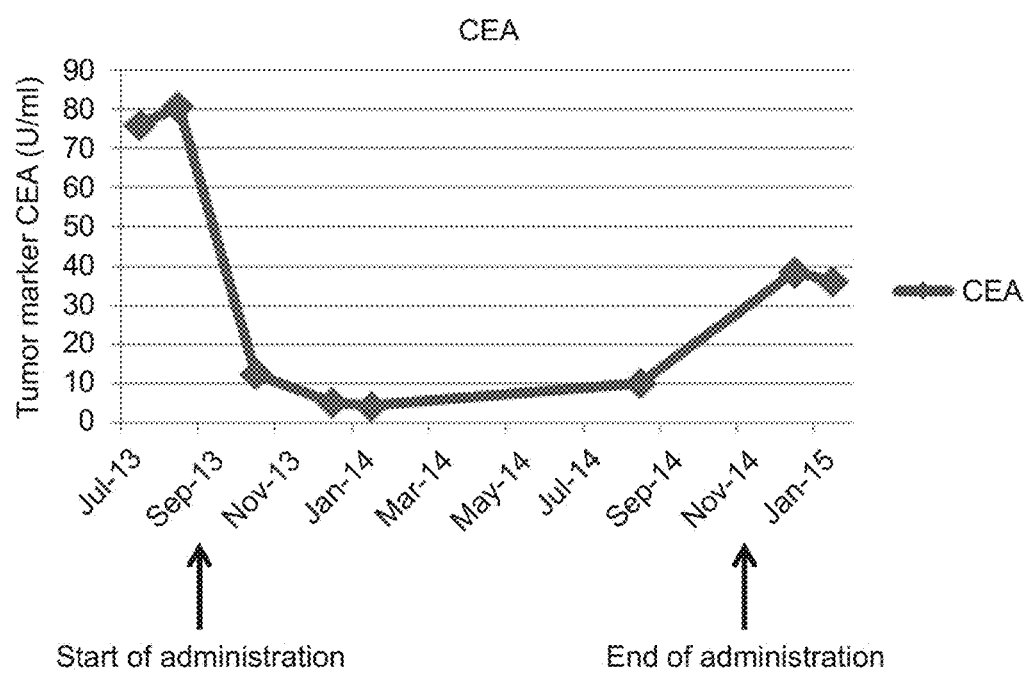
FIG. 11 This figure is a graph showing the changes in CEA in peripheral blood by combination administration of Bestatin and a molecular targeted drug (Xalkori™) on a 30-year-old case of the carcinomatous pleurisy and carcinomatous pericarditis caused by lung cancer.

As a result, a drop in the tumor marker CEA value was confirmed after the start of administration. FIG. 11 shows the measured values of the patient's CEA.

Figure 12:
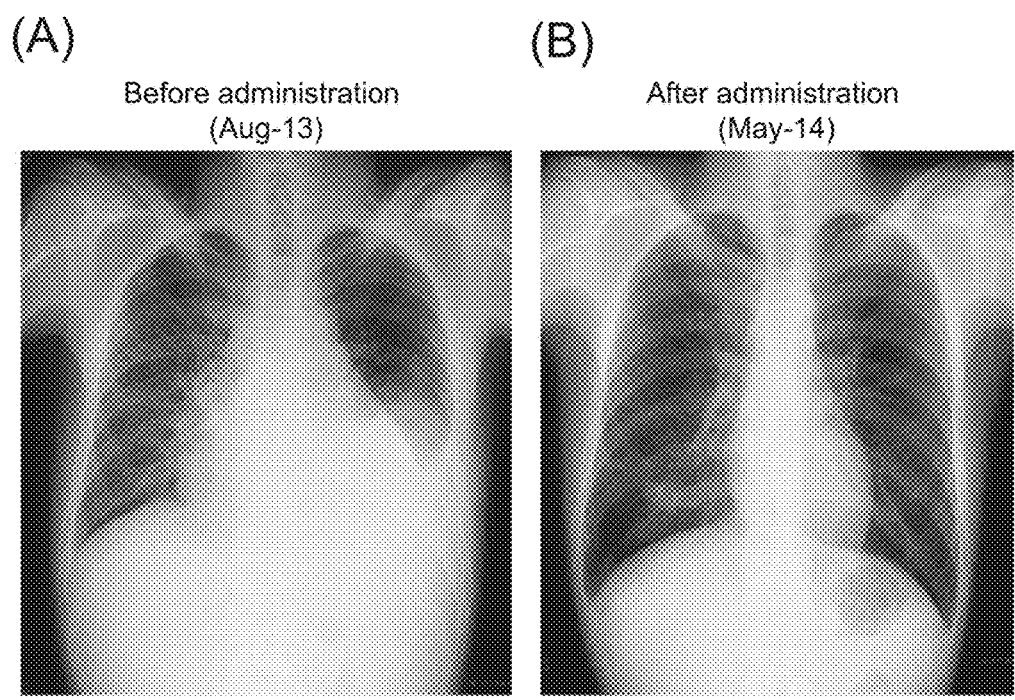
FIG. 12 This figure is photo images (chest X-ray images) showing the focus before (A) and after (B) combination administration of Bestatin and a molecular targeted drug (Xalkori™) on a 30-year-old case of the carcinomatous pleurisy and carcinomatous pericarditis caused by lung cancer.

Further, 9 months later from the start of administration (May 2014), the focuses of carcinomatous pleurisy and carcinomatous pericarditis disappeared or regressed (FIG. 12: chest X-ray images).

Example 11

Combination Administration of Bestatin and Molecular Targeted Drug (Iressa™) on a 73-year-old Case of Lung Adenocarcinoma Bestatin (10 mg/day, once a day every day) and Iressa™ (250 mg/day, 4 days a week) were administered (administration started in the end of April 2014) to a 73-year-old lung adenocarcinoma patient (having a variation in EGFR, with metastasis to the cervical lymph node).

Figure 13:
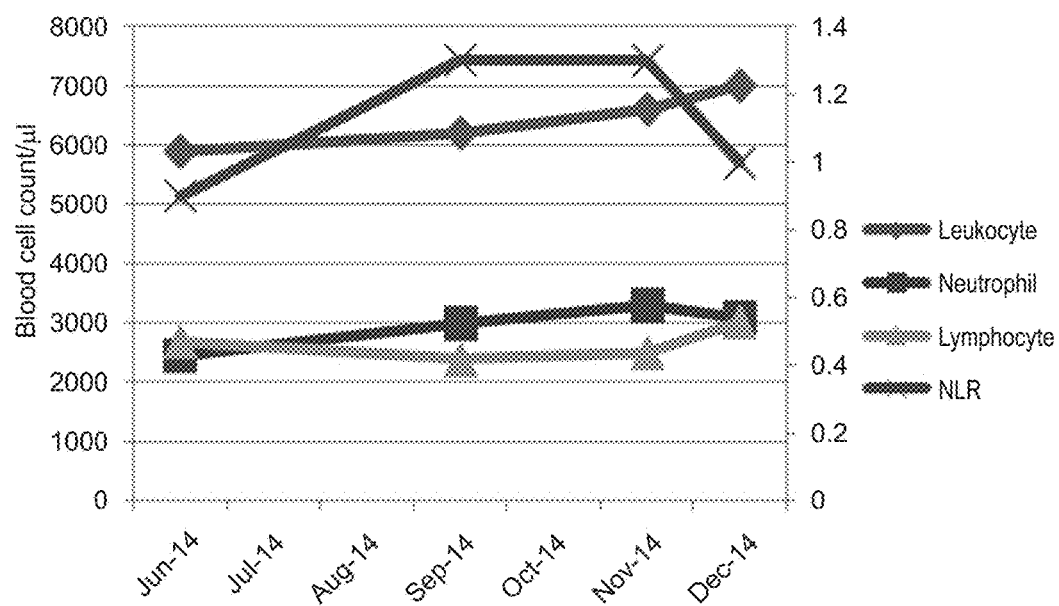
FIG. 13 This figure is a graph showing the changes in leukocytes, neutrophils, lymphocytes and NLR in peripheral blood by combination administration of Bestatin and a molecular targeted drug (Iressa™) on a 73-year-old case of lung adenocarcinoma.
Figure 14:
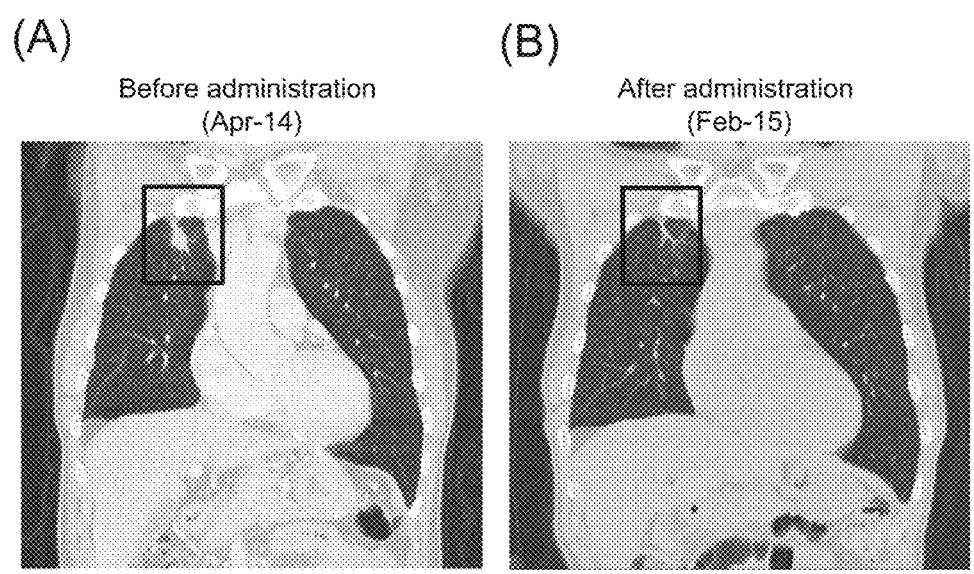
FIG. 14 This figure is photo images (chest X-ray images) showing the focus before (A) and after (3) combination administration of Bestatin and a molecular targeted drug (Iressa™) on a 73-year-old case of lung adenocarcinoma. The square shows the region where treatment effects were notably confirmed.

As a result, the drop and improvement in the NLR value and the increase and improvement in the lymphocyte count were confirmed. FIG. 13 shows the measured values of patient's leukocytes, neutrophils, lymphocytes and NLR. Further, the lung focus was found to have disappeared/regressed (FIG. 14: chest X-ray images).

Example 12

Bestatin and a Molecular Targeted Drug (Tarceva™) Combination Administration on a 71-year-old Case of the Post-surgery Recurrence of Lung Adenocarcinoma Bestatin (10 mg/day) and Tarceva™ (50 mg/day) were administered once a day every day starting from the beginning of January 2015 to a 71-year-old lung adenocarcinoma patient (having a variation in EGFR, and having received a lung left lower lobectomy, then lymphadenectomy in August 2009 and taken an anticancer agent for 2 months after surgery. Thereafter, lung adenocarcinoma recurred in August 2013 and the pleural effusion was confirmed in May 2014).

As a result, drops in the tumor markers CEA and SLY values were confirmed after the start of administration and the urine pH value was also confirmed to have elevated.

Figure 15:
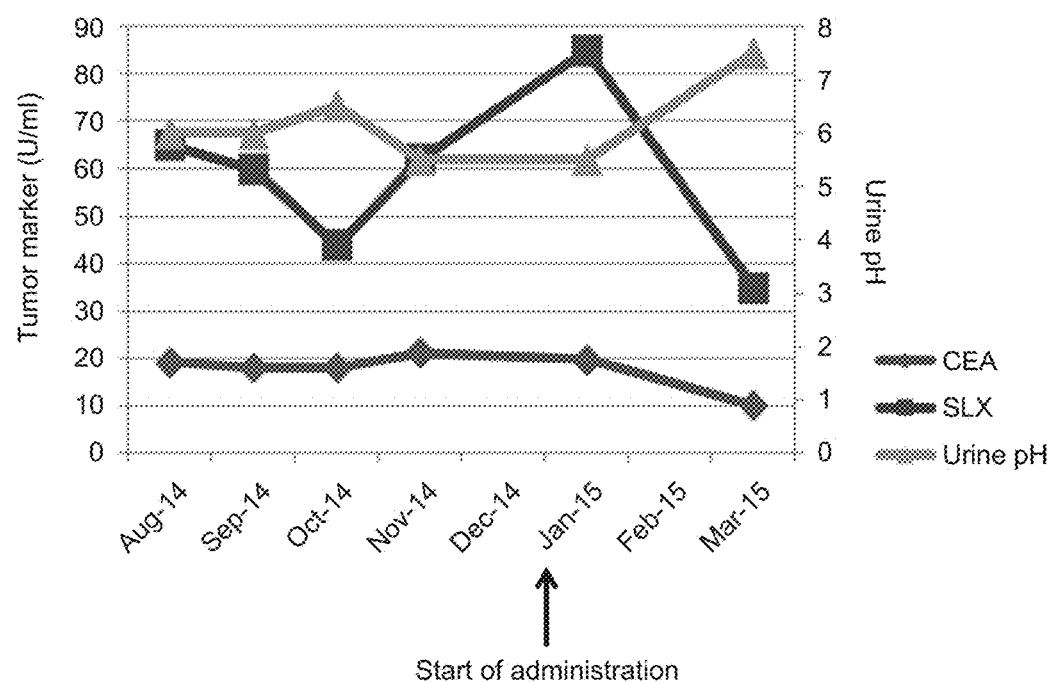
FIG. 15 This figure is a graph showing the changes in CEA and SLX in peripheral blood and the changes in urine pH by combination administration of Bestatin and a molecular targeted drug (Tarceva™) on a 71-year-old case of the post-surgery recurrence of lung adenocarcinoma.

FIG. 15 shows the measured values of the patient's CEA and SLX in peripheral blood and the urine pH. Note that the urine pH tips to the acidic side when a cancer patient's condition is aggravated but is generally known to change to the neutral to alkaline side as the cancer patient's condition recovers and is used as the marker indicating a cancer patient's condition as in the widely used tumor markers.

Example 13

Combination Administration of Bestatin and Molecular Targeted Drug (Tarceva™) on a 66-year-old case of the Multiple Brain Metastases of Lung Adenocarcinoma 3D Irradiation was conducted in December 2014 without cranial irradiation to a 66-year-old terminal lung adenocarcinoma patient (with metastases to the brain, lymph nodes and bones), and subsequently Bestatin (10 mg/day) and Tarceva™ (50 mg/day) were administered to the patient once a day every day (Where the administration was started in January 2015).

Figure 16:
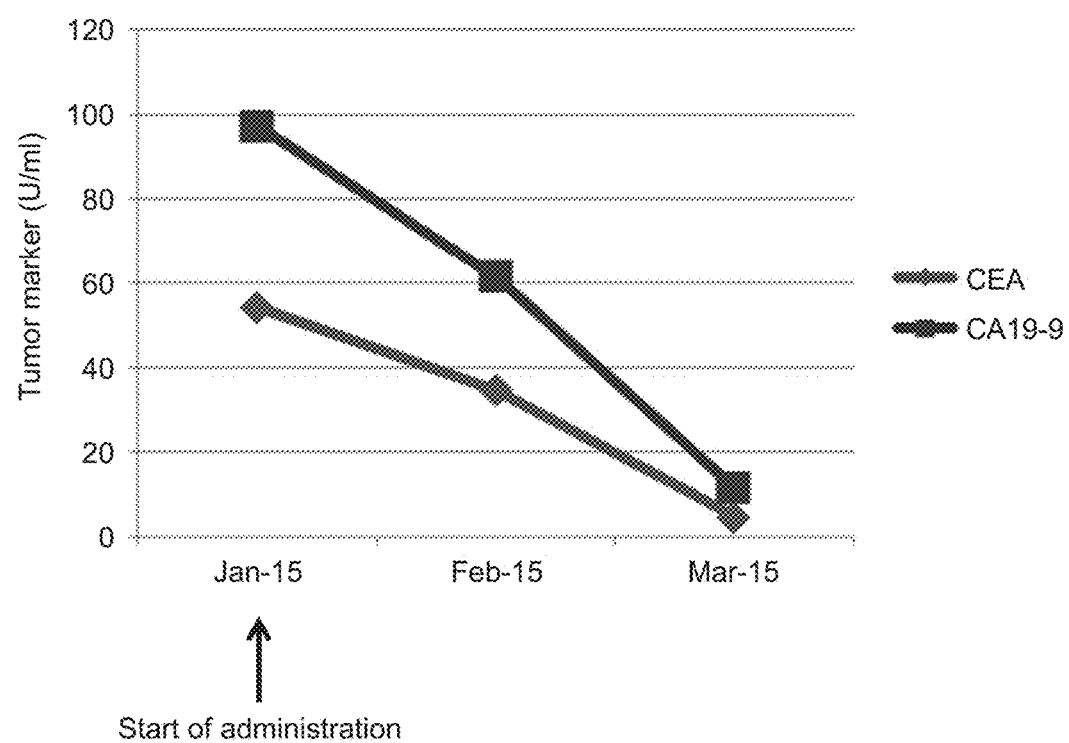
FIG. 16 This figure is a graph showing the changes in CA19-9 and CEA in peripheral blood by combination administration of Bestatin and a molecular targeted drug (Tarceva™) on a 66-year-old case of the multiple brain metastases of lung adenocarcinoma.
Figure 17:
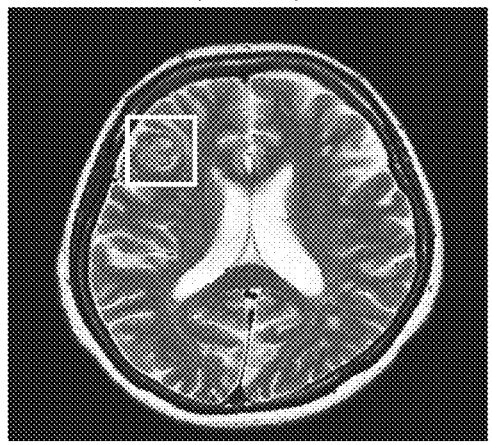
FIG. 17 This figure is photo images (brain MRI diagnostic images) showing the focus before (A) and after (B) combination administration of Bestatin and a molecular targeted drug (Tarceva™) on a 66-year-old case of the multiple brain metastases of lung adenocarcinoma. The square shows the region where treatment effects were notably confirmed.
Figure 17:
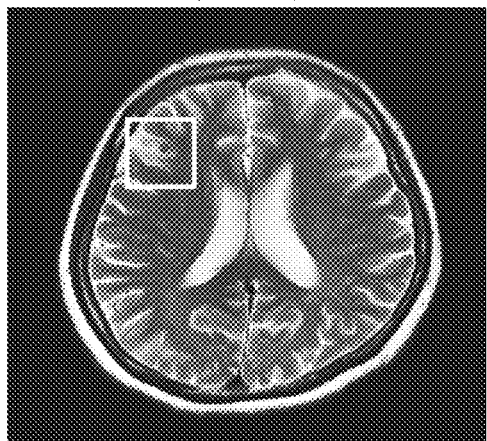

As a result, drops in the patient's tumor markers CA19-9 and CEA values were confirmed. FIG. 16 shows the measured values of the patient's CA19-9 and CEA in peripheral blood. Further, the size and number of the brain metastatic cancer were found to have reduced (FIG. 17: brain MRI diagnostic images).

Example 14

Combination Administration of Bestatin and Molecular Targeted Drug (Giotrif™) on a 66-year-old Case of the Post-surgery Recurrence and Multiple Bone Metastases of Lung Adenocarcinoma Bestatin (10 mg/day) and Giotrif™ (20 mg/day) were administered starting in August 2014 once a day every day to a 66-year-old terminal lung adenocarcinoma patient (having a variation in EGFR, with post-surgery recurrence and metastases to the backbone, etc.).

Figure 18:
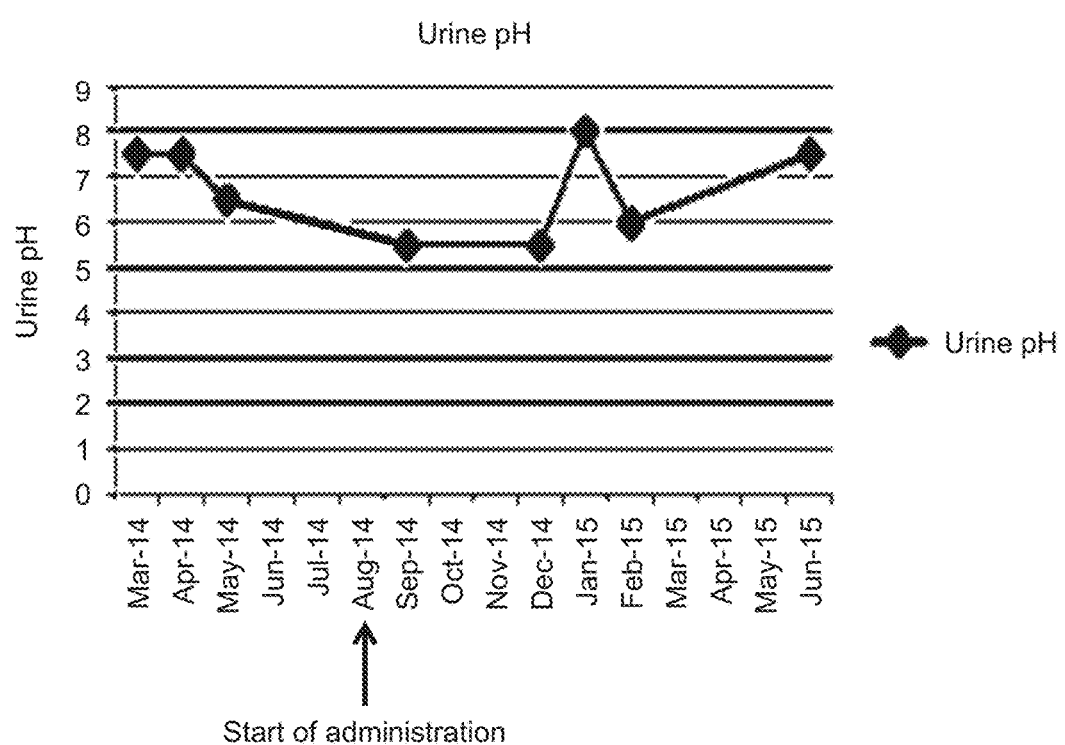
FIG. 18 This figure is a graph showing the changes in urine pH by combination administration of Bestatin and a molecular targeted drug (Giotrif™) on a 66-year-old case of the post-surgery recurrence and multiple bone metastases of lung adenocarcinoma.
Figure 19:
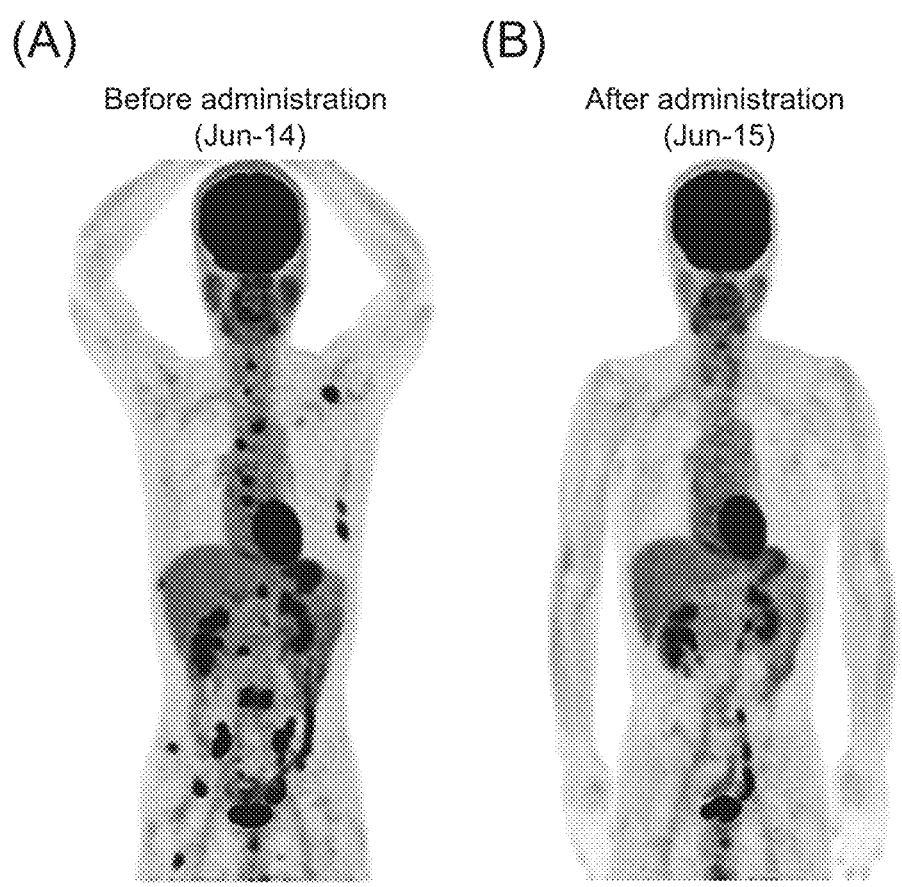
FIG. 19 This figure is photo images (PET diagnostic images) showing the focuses before (A) and after (B) combination administration of Bestatin and a molecular targeted drug (Giotrif™) on a 66-year-old case of the post-surgery recurrence and multiple bone metastases of lung adenocarcinoma FIG. 20 This figure is a graph showing the changes in tumor volume (mm$^3$) in the mice of each group treated with gefitinib and/or Bestatin.

As a result, the patient's urine pH value was found to have elevated (changed to the alkaline side). FIG. 18 shows the measured values of the patient's urine pH. Further, the metastatic cancers including backbone metastasis were found to have disappeared (FIG. 19: PET diagnostic images).

Example 15

Evaluation of Antitumor Effects Attained by Combination of Bestatin and Molecular Targeted Drug

[1] Production of Cancer-Bearing Mouse

A549 human lung carcinoma suspension (5×10⁶ cells/100 μL PBS) was subcutaneously inoculated to BALB/c nu/nu mice (female). After cells were transplanted, mice with a tumor volume reaching about 117 mm³ (on day 15 after the cell transplantation) were used for the following in vivo experiments,

[2] Evaluation of Antitumor Effects Attained by Combination of Bestatin and Gefitinib Bestatin and gefitinib were respectively administered by the following doses, administration route and schedule to the above A549 cancer-bearing mice.

TABLE 4

| Group | Number of individuals | Treatment | Dose (mg/kg)* | Ratio of gefitinib/ Bestatin | Drug administration route/Schedule |
|---|---|---|---|---|---|
| G1 | 6 | PBS (Control) | — | — | po, qd. 6 days/ week × 3 weeks |
| G2 | 6 | gefitinib | 10 | — | po, qd. 6 days/ week × 3 weeks |
| G3 | 6 | Bestatin** | 30 | — | po, qd. 6 days/ week × 3 weeks |
| G4 | 6 | gefitinib Bestatin | 10 0.1 | 100 | po, qd. 6 days/ week × 3 weeks |
| G5 | 6 | gefitinib Bestatin | 10 0.3 | 33 | po, qd. 6 days/ week × 3 weeks |
| G6 | 6 | gefitinib Bestatin | 10 1 | 10 | po, qd. 6 days/ week × 3 weeks |
| G7 | 6 | gefitinib Bestatin | 10 3 | 3.3 | po, qd. 6 days/ week × 3 weeks |
| G8 | 6 | gefitinib Bestatin | 10 10 | 1.0 | po, qd. 6 days/ week × 3 weeks |
| G9 | 6 | gefitinib Bestatin | 10 30 | 0.33 | po, qd. 6 days/ week × 3 weeks |

Note:
*Dose is an amount adjusted based on the body weight of a mouse (10 μL/g).
**Amount of Bestatin is adjusted to 3 mg/mL in PBS.
po: Oral administration
qd: once a day The antitumor effect was examined based on changes in tumor volume and changes in body weight.

The tumor volume was calculated by the following formula.

$$\text{Tumor volume (mm}^3\text{)} = (\text{long side of tumor}) \times (\text{short side of tumor})^2 \times 0.5$$

Tumor growth inhibition (TGI) was also calculated from the tumor volume by the following formula.

TGI (%)=(1-T/C)×100% (wherein T represents a tumor volume (mm³) of the treated group and C represents a tumor volume (mm³) of the control group.)

Figure 20:
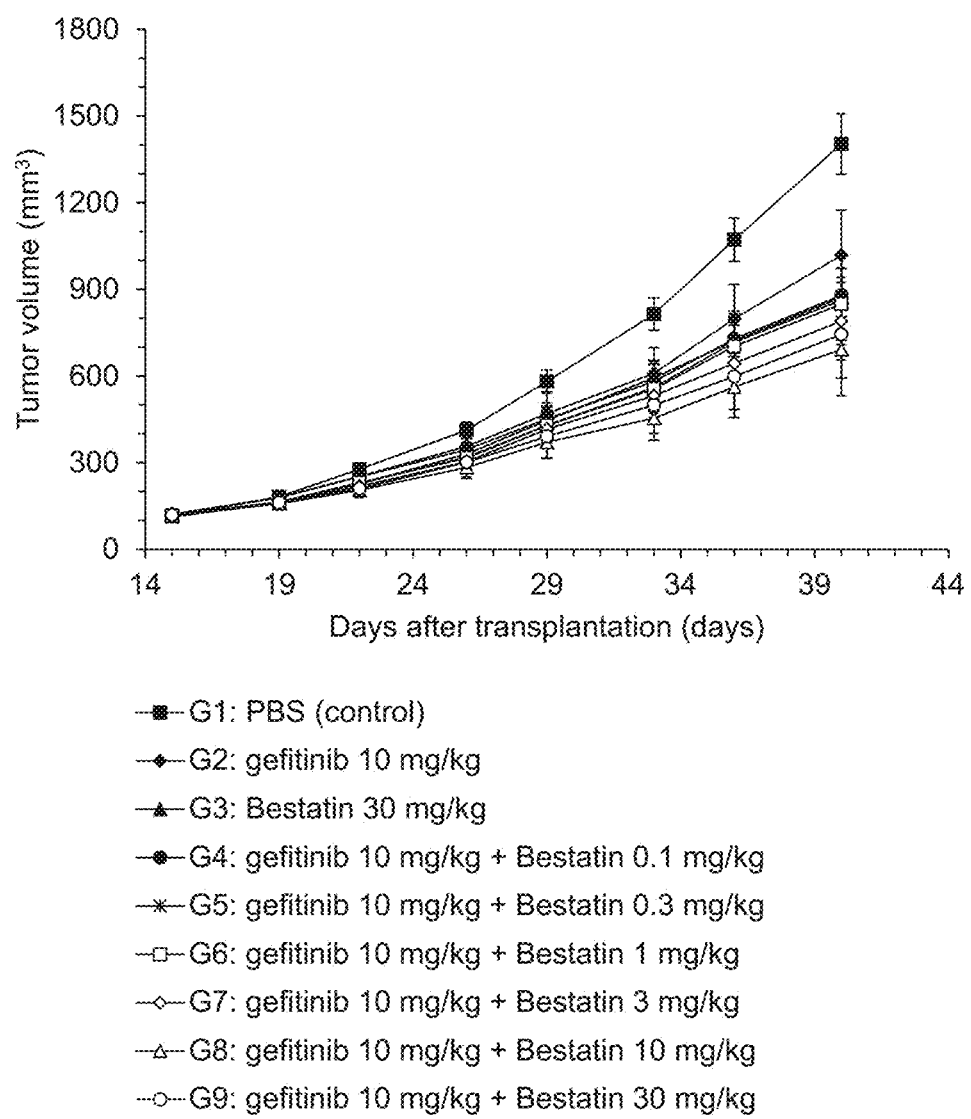

FIG. 20 shows the changes in tumor volumes in each group.

Table 5 below shows TGI of group. P≤0.05 is determined that there is a significant difference.

TABLE 5

| Group | Treatment | TGI (%) On day 40 | p Value (vs. Control (G1)) |
|---|---|---|---|
| G1 | PBS (Control) | — | — |
| G2 | gefitinib 10 mg/kg | 31 | 0.043 |
| G3 | Bestatin 30 mg/kg | 39 | 0.006 |
| G4 | gefitinib 10 mg/kg Bestatin 0.1 mg/kg | 39 | 0.007 |
| G5 | gefitinib 10 mg/kg Bestatin 0.3 mg/kg | 40 | 0.006 |
| G6 | gefitinib 10 mg/kg Bestatin 1 mg/kg | 40 | 0.004 |
| G7 | gefitinib 10 mg/kg Bestatin 3 mg/kg | 44 | 0.002 |
| G8 | gefitinib 10 mg/kg Bestatin 10 mg/kg | 51 | <0.001 |
| G9 | gefitinib 10 mg/kg Bestatin 30 mg/kg | 50 | 0.001 |

When treated with gefitinib alone (10 mg/kg) (G2), TGI (%) was 31% (p=0.043 vs control). When treated with Bestatin alone (30 mg/kg) (G3), TGI (%) was 39% (p=0.006 vs control).

On the other hand, when gefitinib (10 mg/kg) and Bestatin (3, 10 and 30 mg/kg)were combined (G7, G8, G9), comparatively higher TGIs (%) were achieved (each 44%, 51% and 50%) than the cases treated by single administration of gefitinib or Bestatin (G2 or G3).

It was further confirmed that even when gefitinib and Bestatin were used in cot bination, the body weight was not substantially decreased. This indicates that no clinical side effects were confirmed, thereby suggesting that the combination administration of gefitinib and Bestatin is a gentle therapy without involving side effects on cancer patients.

The results confirmed that when Bestatin and gefitinib were administered in combination, a synergistic effect was attained and a notable tumor growth inhibition effect was achieved even with the use of a low gefitinib dose. Such an effect was confirmed to be achieved when Bestatin and gefitinib were administered in combination in a weight ratio of about 1:0.3 to 1:3.

All publications, patents and patent applications cited herein are incorporated by reference in their entirety.

The invention claimed is:

1. A method for treating or putting into remission a patient in need thereof, said method comprising:
    selecting a solid cancer patient aged 70 or more or a terminal solid cancer patient, the patient's neutrophil count to lymphocyte count ratio in peripheral blood being 4 or more or the patient's platelet count to lymphocyte count ratio being 1.5 or more, wherein the peripheral blood of said cancer patient has a normal range of platelet counts or a normal range of neutrophil counts; and
    administering to said patient a composition comprising, as an active ingredient, sufficient (2S)-2- [(2S,3R)-3-amino-2-hydroxy-4-phenylbutanoylamino]-4-methyl-pentanoic acid or a pharmacologically acceptable salt thereof to provide said patient with a dosage 10 mg/body/day.

2. The method of claim 1, which additionally comprises administering to said patient a sufficient amount of an anticancer agent or a molecular targeted drug to provide said patient with a dosage in the range from 0.0001 mg to 1000 mg/body/day.

* * * * *